United States Patent [19]

Akers et al.

[11] Patent Number: 4,806,487

[45] Date of Patent: Feb. 21, 1989

[54] BASIC DRUG DETECTION METHOD

[75] Inventors: Susan Akers, Mantua; Raymond F. Akers, Jr., Cherry Hill, both of N.J.

[73] Assignee: Analytical Innovations, Inc., Cherry Hill, N.J.

[21] Appl. No.: 55,437

[22] Filed: May 29, 1987

[51] Int. Cl.$^4$ .................... G01N 21/78; G01N 33/94
[52] U.S. Cl. ........................ 436/93; 436/92;
436/96; 436/98; 436/169; 436/170; 436/178; 436/901
[58] Field of Search ............ 436/92, 93, 96, 98, 436/131, 164, 169, 170, 178, 901

[56] References Cited

U.S. PATENT DOCUMENTS

| | | |
|---|---|---|
| 2,865,718 | 12/1958 | Fowler . |
| 3,275,416 | 9/1966 | Zaar et al. .............................. 436/98 |
| 3,598,533 | 8/1971 | Tomioka . |
| 3,625,652 | 12/1971 | Fujimoto et al. ................. 436/92 X |
| 3,802,842 | 4/1974 | Lange . |
| 3,901,657 | 8/1975 | Lightfoot . |
| 3,915,639 | 10/1975 | Friedenberg ................... 436/901 X |
| 3,966,410 | 6/1976 | Jahnsen ............................ 436/901 X |
| 4,104,027 | 8/1978 | Carroll .................................. 436/92 |
| 4,196,167 | 4/1980 | Olson . |
| 4,393,141 | 7/1983 | Schlueter et al. ................ 436/178 X |
| 4,438,067 | 3/1984 | Siddiqi . |
| 4,680,120 | 7/1987 | Ramsden et al. ............... 436/901 X |
| 4,680,121 | 7/1987 | Ramsden et al. ............... 436/901 X |

FOREIGN PATENT DOCUMENTS 1426177 2/1976 United Kingdom .................. 436/92

OTHER PUBLICATIONS

Lau-Cam et al., J. of Pharmaceutical Sciences, vol. 68, No. 8, pp. 976–978, 1979.
De Faubert Maunder, Bulletin on Narcotics, vol. XXVI, No. 4, pp. 19–26, 1974.
De Faubert Maunder, J. of Chromatography, vol. 100, pp. 196–199, 1974.
De Faubert Maunder, J.A.P.A., vol. 7, pp. 24–30, 1969.
De Faubert Maunder, J. Pharm. Pharmac., vol. 21, pp. 334–335, 1969.

Primary Examiner—Barry S. Richman
Assistant Examiner—Robert J. Hill, Jr.
Attorney, Agent, or Firm—Steele, Gould & Fried

[57] ABSTRACT

A method for detecting basic narcotics or drugs in body fluids which comprises filtering body fluids through a cellulosic filtering means treated with a binding agent for the narcotics or drugs and the filtering means. The binding agent is a polycarboxylic acid. The narcotics or drugs are then treated with a subsequent reagent to produce a color reaction. A device for detecting basic narcotics or drugs in also disclosed which contains the filtering means treated with the binding agent so as to concentrate the narcotic or drug prior to reaction with a suitable indicator.

9 Claims, 1 Drawing Sheet

BASIC DRUG DETECTION METHOD

FIELD OF THE INVENTION

The present invention relates to testing methods used to ascertain the presence of certain types of basic narcotics or drugs in body fluids. More particularly, the invention is concerned with a method for concentrating such basic drugs that may be present in urine and detecting their presence colorimetrically by a suitable chemical reagent.

BACKGROUND OF THE INVENTION

Due to the wide spread use of controlled substances or narcotics such as morphine, cocaine, amphetamines, tranquilizers, synthetic analgesics, and the like, it has become desirable to institute drug testing of athletes and others which are engaged in an occupation involving a public trust or in which an injury can occur if the party is not completely alert. Testing of athletic teams, bus drivers, etc. involve large group testing which must be conducted quickly, accurately and inexpensively. A highly sensitive, easily-read test for the detection of narcotics such as heroin in urine would be extremely helpful in a drug program. Narcotic screening has become extensive practice in industry, business, the Armed Forces, schools and in the courts and prison systems. Such screening is used both as a pre-employment procedure and as a monitoring tool. The present methods for the detection of these basic narcotics in urine are relatively costly and time consuming and must, in general, be performed by qualified personnel in well-equipped laboratories. It would be highly desirable and useful to be able to carry out a quick test of the presence of such narcotics in urine by a person who is untrained in chemical laboratory manipulations and who does not have at his disposal the instrumentation and laboratory equipment required in the present methods. The validity of such a test method must have a sensitivity to morphine in urine of approximately 1 microgram per milliliter of solution and must not require more than 23 to 50 milliliters of urine.

Clarke, "Isolation and Identification of Drugs", The Pharmaceutical Press, London, 1969, pp 431–432, which is herein incorporated by reference discloses chemical reagents which can be utilized in the detection of common narcotic substances.

OBJECTS AND SUMMARY OF THE INVENTION

It is an object of this invention to provide a method for the detection of a basic narcotic substance including tranquilizers and other CNS (Central Nervous System) drugs present in minute amounts in body fluids.

It is another object of the present invention to provide a method which is broadly adaptable to a wide variety of colorimetric reactions and which will increase the sensitivity of the color reaction in drug testing by several fold over the corresponding solution reaction.

It is a further object of this invention to provide a method capable of rapidly and colorimetrically detecting, in the hands of untrained people, extremely minute amounts of a basic narcotic substance in urine.

It is a still further object of the invention to detect the presence of a multiplicity of narcotic substances or CNS affecting compounds in body fluids of mammals.

These and other objects of the invention can be achieved by providing a cellulosic filtering means which is treated with a binding agent and a suitable chemical detecting reagent. The filtering means serves to collect, and therefore to concentrate any basic drug or narcotic which may be present in the body fluids and which may be too dilute to be detected by conventional techniques. It is particularly advantageous in detecting narcotic or drug use where the drug user has abstained from drug use for a few days in anticipation of the test.

The filtering means of the present invention in essence filters the narcotic or drug from urine that is passed through the filtering means by binding these narcotics or drugs through a binding agent for the filtering means and the narcotic or drug. The chemical reagent for the particular narcotic being detected is then poured onto the filtering means, and a characteristic color appears which indicates that the narcotic or drug is present.

Advantageously, the filtering means is used in connection with a funneling means so as to facilitate collection and concentration at the disk. The body fluid or urine sample is first poured onto a disk impregnated with a suitable binding agent, and then a suitable chemical reagent is poured over the disk. A characteristic color appears on the disk indicating whether or not a narcotic or drug is present.

Among the various basic narcotics or drugs which may be detected are cocaine, morphine, heroin, amphetamines, phencyclidine, PCP, chlordiazepoxide, propoxphene, synthetic analgesics, alkaloids, catecholamines, etc.

The binding agent which is utilizable in the present invention is a polycarboxylic acid compound wherein at least one of the carboxylic acid groups binds with the free hydroxyl groups of the cellulosic material. The filtering means and another carboxylic acid group binds with a basic group of a narcotic being tested. Preferably, the polycarboxylic acid compounds are compounds of the formula:

$$HOOC-R-COOH \qquad (I)$$

wherein R is selected from the group consisting of a cycloalkyl of 4 to 6 carbon atoms, alkyl of 2 to 12 carbon atoms, alkylene of 2 to 12 carbon atoms, heterocyclic of five or six carbon atoms and phenyl.

The suitable acids which may be used as the binding agent include maleic acid, fumaric acid, adipic acid, succinic acid, phthalic acid, etc.

Reagents which interact with the basic narcotic or drug to produce a color reaction include cobaltous thiocyanate and tetrabromophenolphthalein ethyl ester.

Other objects and a fuller understanding of the invention will be had by referring to the following description and claims of a preferred embodiment, taken in conjunction with the accompanying drawings, wherein like reference characters refer to similar parts throughout the several views.

DESCRIPTION OF THE PREFERRED EMBODIMENT OF THE INVENTION

Figure 1:
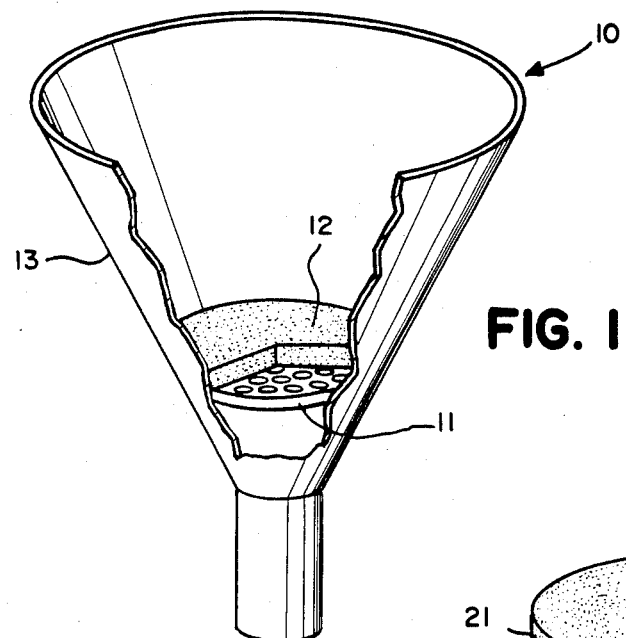
FIG. 1 is a perspective view of the testing device of the invention.

Although specific terms are used in the following description for the sake of clarity, these terms are intended to refer only to the particular structure of the invention selected for illustration in the drawings, and are not intended to define or limit the scope of the invention.

As illustrated in FIG. 1, the test device of the invention may comprise a means 10 for collecting and concentrating body fluids, for example, urine, for testing for the presence of basic narcotics and drugs. The means 10 may, for example, comprise a funnel 13 having a perforated support 11 on which there is placed a cellulosic disk 12. A binding agent is placed into solution and poured through the funnel 13 so as to bind on the disk 12. The test fluid which is suspected of containing a narcotic or drug is then passed through the funnel 13 whereby the narcotic or drug interacts with the binding agent and remains on the disk. A suitable test reagent for the narcotic or drug is poured through the funnel and the development of a specific color on the disk indicates the presence of a narcotic or drug.

The disk 12 can consist of cellulosic filter paper or regularly woven cellulosic filaments in the form of a fabric with weft and warp threads or can be in the form of an unwoven fabric. It is also possible to use thin felt-or fleece-like meshwork in which the fibre structure is not uniform, provided that they have the necessary neutral color and stability. It is preferred to use natural cellulosic material or anionic synthetic resin fabric of monofile or spun filaments which can consist of cellulose materials, for example cotton, cellulose, carboxymethyl cellulose, flax or sisal. Within the given limits, the meshwork can be varied, depending upon the color reaction of the indicator layer. Normally, a meshwork of colorless material is used. However, with colored meshwork, mixed colors with the colors of the indicator layer, are obtained which can sometimes increase the contrast. In addition, it is also possible to impregnate the meshwork with reagents which only penetrate into the indicator layer upon wetting. This separate impregnation is recommended when there is a possibility that two or more binding agents, detection reagents and/or adjuvants might react together during storage.

Figure 2:
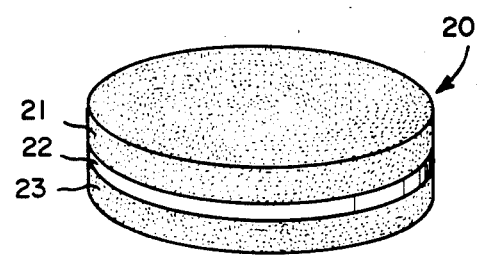
FIG. 2 is a schematic presentation of a specific embodiment of a multi-layered disk of the invention.

As shown in FIG. 2, the disk used in concentrating the narcotic or drug may comprise a multi-layered disk 20. The first layer 21 may be a cellulosic layer treated with a binding agent for the layer and for a basic narcotic or drug. The second layer 23 may be associated with the first layer 21 through a neutral boundary layer 22 which prevents interaction between the different chemical reagents.

The second layer 23 may be a second cellulosic layer impregnated with an acidic organic indicator for cannabinoids, such as Fast Blue BB. After a body fluid is filtered through the disk 20, the second layer 23 will change color when cannabinoids are present in the body fluid. An indicator for basic narcotics or drugs is then added to the first layer to develop a color change therein when a basic narcotic or drug is present in the body fluid. The multilayered disk is advantageous for use when the testing of the narcotic in the body fluids includes tests for cannabinoids or tranquilizers and other basic drugs such as heroin. In such a case, one layer can test for the cannabinoids or tranquilizers and the other lay can test for other narcotics.

Figure 3:
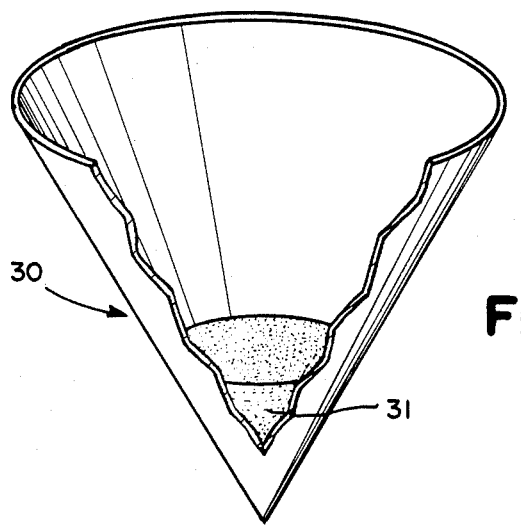
FIG. 3 is a side sectional view of a disposable test funnel having a reagent impregnated portion.

FIG. 3 illustrates a filter 30 which is impregnated in part 31 with a binding agent. The filter 30 is intended for use with a conventional funnel. After urine is passed through the funnel, an indicator is added and the color is observed to indicate the presence of a narcotic or drug.

The indicators which may be utilized in the invention are known and commercially available. These indicators include the following:

| Indicator | Chemical Composition | Drug or Narcotic Tested |
|---|---|---|
| Marquis Reagent | Formaldehyde in $H_2SO_4$ | Opiates, amphetamines, diazepam, phenothiazines, propoxphenes |
| Mecke Reagent | Selenious acid in $H_2SO_4$ | Opiates, mescaline, amphetamines |
| Froehde Reagent | Molybdic acid in $H_2SO_4$ | Opiates, mescaline, amphetamines |
| Iodoplatinate Reagent | Platinic chloride and potassium iodide | Opiates, PCP, cocaine, amphetamines, propoxphenes, benzodiazepines |
| Mandelin Reagent | Ammonium vandate in $H_2SO_4$ | Opiates, amphetamines, mescaline, phenothiazines |

From the foregoing it is believed that those familiar with the art will readily recognize and appreciate the novel concepts and features of the present invention. Numerous variations, changes and substitutions of equivalents will present themselves from persons skilled in the art and may be made without necessarily departing from the scope and principles of this invention. As a result, the embodiment described herein is subject to various modifications, changes and the like, with the scope of this invention being determined solely by reference to the claims appended hereto.

What is claimed is:

1. A method for analyzing a sample of a body fluid for the presence of a basic drug which comprises:
    filtering a sample of a body fluid through a cellulosic filtering means which has been treated with a binding agent for said filtering means and a basic drug so that any of said basic drug in said sample binds to said filtering means, said binding agent being a compound having the formula

HOOC—R—COOH wherein R is selected from the group consisting of a cycloalkyl group having 4 to 6 carbon atoms, an alkyl group having 2 to 12 carbon atoms, an alkylene group having 2 to 12 carbon atoms, a heterocyclic group having five or six carbon atoms, and a phenyl group;
    contacting said filtering means with a color indicator for said basic drug; and
    observing the filtering means for any color change, wherein any color change is indicative of the presence of said basic drug in said sample.

2. The method of claim 1 wherein said binding agent is maleic acid.

3. The method of claim 1 wherein said binding agent is adipic acid.

4. The method of claim 1 wherein said body fluid is urine.

5. The method of claim 1 wherein said color indicator is selected from the group consisting of cobaltous thiocyanate and tetrabromophenolphthalein ethyl ester.

6. The method of claim 1 wherein said filtering means is a filtering disk.

7. The method of claim 6 wherein said disk comprises a plurality of layers, at least one of said layers being a cellulosic layer treated with said binding agent.

8. A method for analyzing a sample of a body fluid for the presence of cannabinoids and a basic drug which comprises:

filtering a sample of a body fluid through a filtering means comprising a first cellulosic layer which has been treated with a binding agent for said first cellulosic layer and a basic drug and a second cellulosic layer impregnated with an acidic organic indicator for cannabinoids so that any of said basic drug in said sample binds to said first cellulosic layer and any cannabinoids in said sample reacts with said acidic organic indicator in said second cellulosic layer to produce a color change, said binding agent being a compound having the formula

HOOC—R—COOH wherein R is selected from the group consisting of a cycloalkyl group having 4 to 6 carbon atoms, an alkyl group having 2 to 12 carbon atoms, an alkylene group having 2 to 12 carbon atoms, a heterocyclic group having five or six carbon atoms, and a phenyl group;

observing the second cellulosic layer for any color change, wherein any color change is indicative of the presence of cannabinoids in said sample;

contacting said first cellulosic layer with a color indicator for said basic drug; and observing the first cellulosic layer for any color change, wherein any color change is indicative of the presence of said basic drug in said sample.

9. The method of claim 8 wherein said acidic organic indicator is Fast Blue BB.

* * * * *